(12) United States Patent
Wobbe et al.

(10) Patent No.: US 9,285,392 B1
(45) Date of Patent: Mar. 15, 2016

(54) FIXTURE FOR TESTING FLEXIBLE CIRCUIT

(71) Applicant: Seagate Technology LLC, Cupertino, CA (US)

(72) Inventors: David G. Wobbe, Wabasha, MN (US); David G. Qualey, Apple Valley, MN (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 421 days.

(21) Appl. No.: 13/873,478

(22) Filed: Apr. 30, 2013

(51) Int. Cl.
*G01R 31/00* (2006.01)
*G01R 1/04* (2006.01)
*G01N 27/90* (2006.01)
*G01N 27/82* (2006.01)

(52) U.S. Cl.
CPC .............. *G01R 1/0408* (2013.01); *G01N 27/82* (2013.01); *G01N 27/902* (2013.01)

(58) Field of Classification Search
CPC ........ G11B 5/486; G11B 5/4853; G11B 5/40; G11B 5/484; G11B 5/4826; G11B 5/4833; G11B 5/455; G11B 5/012; G11B 5/3166; G01R 31/2893; G01R 31/2886; G01R 31/2889; G01R 31/2887; G01R 1/0408; G01R 1/04; G01R 1/2851; G01N 27/902; G01N 27/82; G01N 27/9033; G01N 27/455; G01N 27/9093
USPC ........ 324/262, 210, 756.07, 756.01; 360/245, 360/245.1–245.9, 244.1–244.9, 265.9, 266, 360/266.1
See application file for complete search history.

(56) References Cited

U.S. PATENT DOCUMENTS

| | | | | |
|---|---|---|---|---|
| 5,844,420 | A * | 12/1998 | Weber ................. | G11B 5/4806 324/754.03 |
| 6,310,747 | B1 * | 10/2001 | Emo ........................ | G11B 5/11 360/97.21 |
| 6,459,260 | B1 | 10/2002 | Bonin et al. | |
| 6,826,016 | B2 * | 11/2004 | Katsumata ............. | G11B 5/486 360/245.9 |
| 7,014,474 | B2 * | 3/2006 | Wu et al. ........................ | 439/66 |
| 7,509,224 | B2 | 3/2009 | Holwell et al. | |
| 7,529,635 | B2 | 5/2009 | Anderson et al. | |
| 7,684,948 | B2 | 3/2010 | Holwell et al. | |
| 7,805,830 | B2 | 10/2010 | Herdendorf et al. | |
| 8,094,414 | B1 | 1/2012 | Cheng et al. | |
| 8,098,460 | B1 | 1/2012 | Jen et al. | |
| 8,300,361 | B2 | 10/2012 | Boutaghou et al. | |
| 8,379,348 | B2 | 2/2013 | Boutaghou et al. | |
| 8,395,864 | B2 | 3/2013 | Boutaghou et al. | |
| 2003/0165033 | A1 * | 9/2003 | Sasaki .................. | G11B 5/5569 360/265.9 |
| 2006/0006895 | A1 * | 1/2006 | Zhao et al. ..................... | 324/757 |
| 2009/0323212 | A1 * | 12/2009 | Sugiyama ............ | G11B 5/4555 360/31 |
| 2012/0200287 | A1 * | 8/2012 | Warn et al. .................... | 324/212 |

* cited by examiner

Primary Examiner — Tung X Nguyen
Assistant Examiner — Thang Le
(74) Attorney, Agent, or Firm — HolzerIPLaw, PC

(57) ABSTRACT

A test fixture for testing a head gimbal assembly having a flex circuit with a plurality of circuit pads, prior to installation of the head gimbal assembly into a disc drive. The fixture comprises a contact board having a plurality of electrically conductive contact points on a surface thereof, the contact points arranged to contact the circuit pads of the flex circuit. The fixture further comprises a clamp assembly connected to the contact board, the clamp assembly having an activation end, an opposite engagement end, and a pivot axis extending orthogonal to an axis defined by the activation end and the engagement end. The engagement end has a non-conductive engagement surface configured to contact the head gimbal assembly on a surface opposite the plurality of circuit pads.

20 Claims, 6 Drawing Sheets

FIXTURE FOR TESTING FLEXIBLE CIRCUIT

BACKGROUND

Hard disc drives (HDD) and hard disc drive systems typically include one or more data storage discs and a magnetic transducing head carried by a slider to read from and write to a data track on a disc. The transducing head and slider are part of a head gimbal assembly (HGA).

Prior to attaching the HGA into the hard disc drive, it is desirable to dynamically test the functionality of the read and write transducers so that defective HGAs may be identified. Such testing can include preliminary activities to align, configure, and prepare the HGA for testing, followed by the actual electrical test of the HGA. Because HGAs are typically small, fragile and contain sensitive electronic components, they are susceptible to mechanical stress, electro-static discharge, environmental contamination, and other handling-related issues.

Various fixtures for mounting the HGA for testing are known.

SUMMARY

The present disclosure provides a fixture and methods for testing flexible circuits of head gimbal assemblies.

One particular embodiment of this disclosure is a test fixture for testing a head gimbal assembly having a flex circuit with a plurality of circuit pads. The fixture comprises a contact board having a plurality of electrically conductive contact points on a surface thereof; the contact points arranged to contact the circuit pads of the flex circuit, each of the contact points comprising a gold surface and having a height above the surface of the contact board of no more than 8 micrometers. The fixture further comprises a clamp assembly connected to the contact board, the clamp assembly having an activation end, an opposite engagement end, and a pivot axis extending orthogonal to an axis defined by the activation end and the engagement end. The engagement end has a non-conductive engagement surface configured to contact the head gimbal assembly on a surface opposite the plurality of circuit pads, the engagement surface extending at an angle between 0 and 45 degrees to the pivot axis.

Another particular embodiment of this disclosure is a test fixture for testing a head gimbal assembly having a flex circuit with a plurality of circuit pads. The fixture comprises a contact board having a plurality of electrically conductive contact points on a surface thereof, the contact points comprising a dome structure comprising copper and a gold surface, and a clamp assembly connected to the contact board. The clamp assembly has an activation end, an opposite engagement end having a non-conductive engagement surface, and a pivot axis extending orthogonal to an axis defined by the activation end and the engagement end, with the non-conductive engagement surface having a width of no more than 250 micrometers.

Yet another particular embodiment of this disclosure is a test fixture for testing a head gimbal assembly having a flex circuit with a plurality of circuit pads. The fixture comprises a contact board having a plurality of electrically conductive contact points on a surface thereof, the contact points comprising a dome structure comprising a gold surface, and, a non-conductive clamp assembly pivotally connected to the contact board, the clamp assembly having an activation end, an opposite engagement end having an engagement surface, and a pivot axis extending orthogonal to an axis defined by the activation end and the engagement end. Adjacent contact points have a distance of no more than 500 micrometers therebetween, and each of the contact points has a diameter of 200-300 micrometers.

These and various other features and advantages will be apparent from a reading of the following detailed description.

BRIEF DESCRIPTION OF THE DRAWING

The disclosure may be more completely understood in consideration of the following detailed description of various embodiments of the disclosure in connection with the accompanying drawing, in which.

DETAILED DESCRIPTION

The present description is directed to a non-destructive testing device or fixture for holding a head gimbal assembly (HGA) during electrical testing prior to the HGA being incorporated into a disc drive device or data storage device.

In the following description, reference is made to the accompanying drawing that forms a part hereof and in which are shown by way of illustration at least one specific embodiment. The following description provides additional specific embodiments. It is to be understood that other embodiments are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples provided below.

Unless otherwise indicated, all numbers expressing feature sizes, amounts, and physical properties are to be understood as being modified by the term "about." Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", "on top", etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above those other elements.

Figure 1:
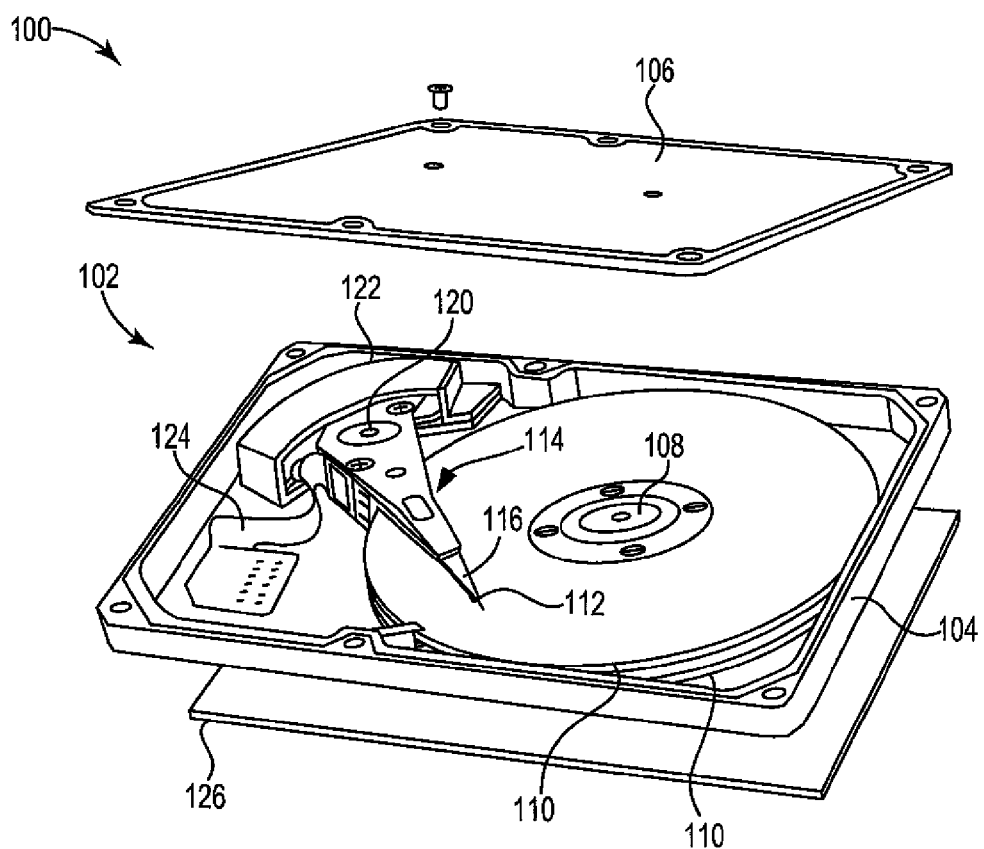
FIG. 1 is an exploded, perspective view of a data storage device.

Referring to FIG. 1, a top perspective view of a disc drive or data storage device 100 is shown. Device 100 includes a sealed housing 102 formed from a base deck 104 and top cover 106. A spindle motor 108 is configured to rotate at least one storage medium such as a disc, in many embodiments multiple storage media or discs 110. Discs 110 are accessed by a corresponding array of data transducers that are each supported by a head gimbal assembly (HGA) 112 supported by a rigid actuator arm 114. Each actuator arm 114 (also referred to as an actuator) includes a flexible suspension assembly 116, often referred to as a load beam. Actuator arm 114 pivots about a cartridge bearing assembly 120 through application of current to a voice coil motor (VCM) 122. In this way, controlled operation of VCM 122 causes the transducers of HGA 112 to align with tracks (not shown) defined on the disc surfaces to store data thereto or retrieve data therefrom.

While FIG. 1 shows the use of two magnetic recording discs and four corresponding heads, other numbers of heads and discs (such as a single disc, etc.) and other types of media (such as optical media, etc.) can alternatively be utilized as desired.

A printed circuit cable 124 provides electrical communication between HGA 112 and actuator 114 and device control electronics on an externally disposed device printed circuit board (PCB) 126. Printed circuit cable 124 includes multiple circuits that allow communication of several different components of device 100 with PCB 126.

Figure 2:
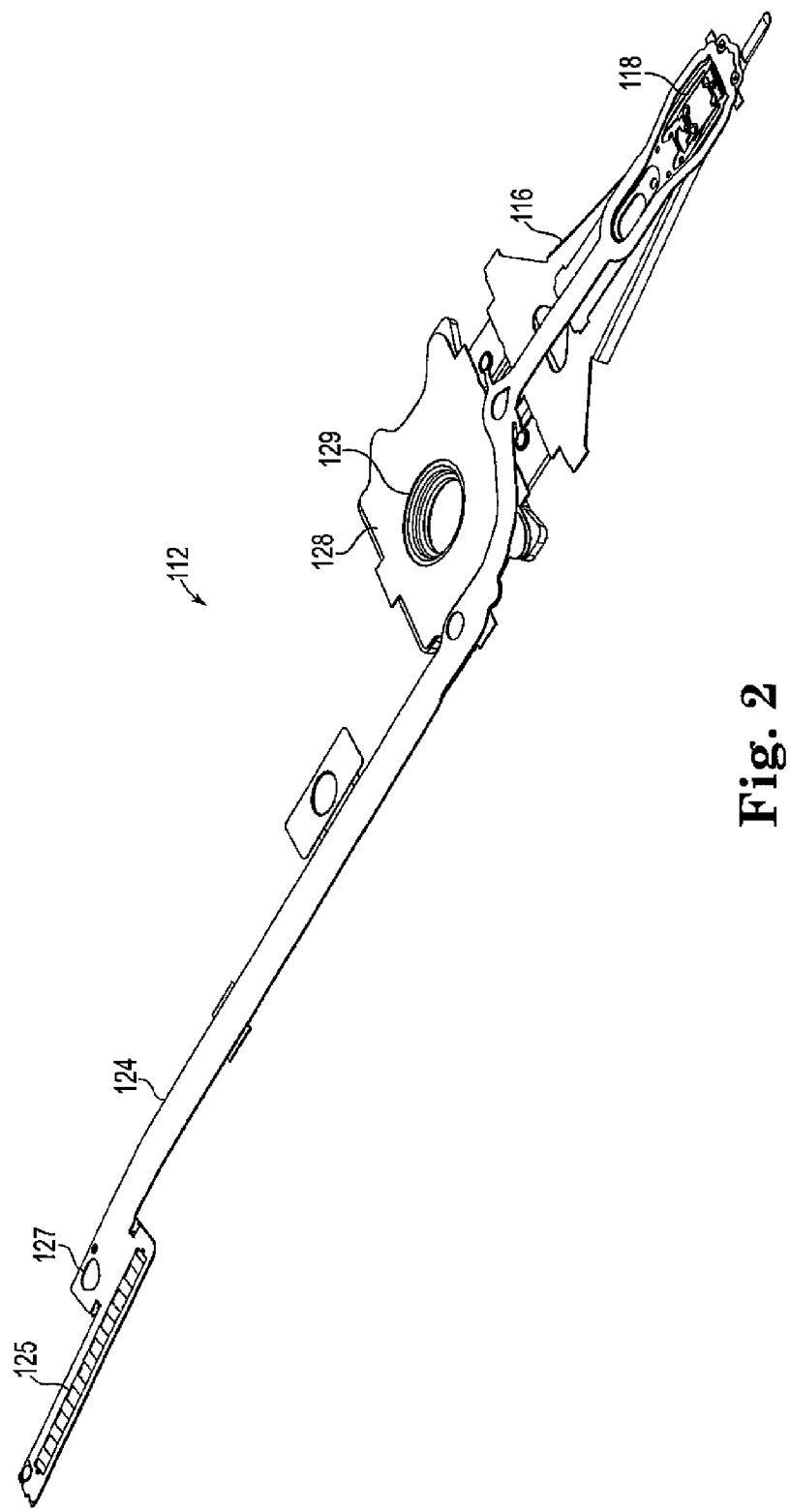
FIG. 2 is a perspective view of an embodiment of an HGA.

As shown in FIG. 2, the basic components of HGA 112 are flexible suspension assembly or load beam 116 supporting a transducing head 118 having read and write transducers, a base plate 128, a boss hole 129, and flex circuit cable 124 with flex circuit pad(s) 125 that connect with PCB 126 (FIG. 1). This embodiment of HGA 112 includes an alignment hole 127, a purpose of which is described below. When installed in disc drive 100 and in use, head 118 'flies' above the surface of disc 110 with the read and write transducers positioned to read and/or write data to disc 110. Load beam 116 is a thin, typically metal structure configured to hold head 118 adjacent to and properly aligned with disc 110 during operation.

After formation of, but prior to installation of HGA 112 into disc drive 100, HGA 112 is dynamically tested to confirm the functionality of the various circuits thereon, the functionality of the read and write transducers, and to identify any otherwise defective HGA 112. During this testing, the electrical connection and functionally from head 118 to flex circuit pad(s) 125 is tested. The following discussion provides various embodiments of a fixture for holding HGA 112 for the dynamic testing. The fixture properly aligns and holds HGA 112 during the test.

Figure 3:
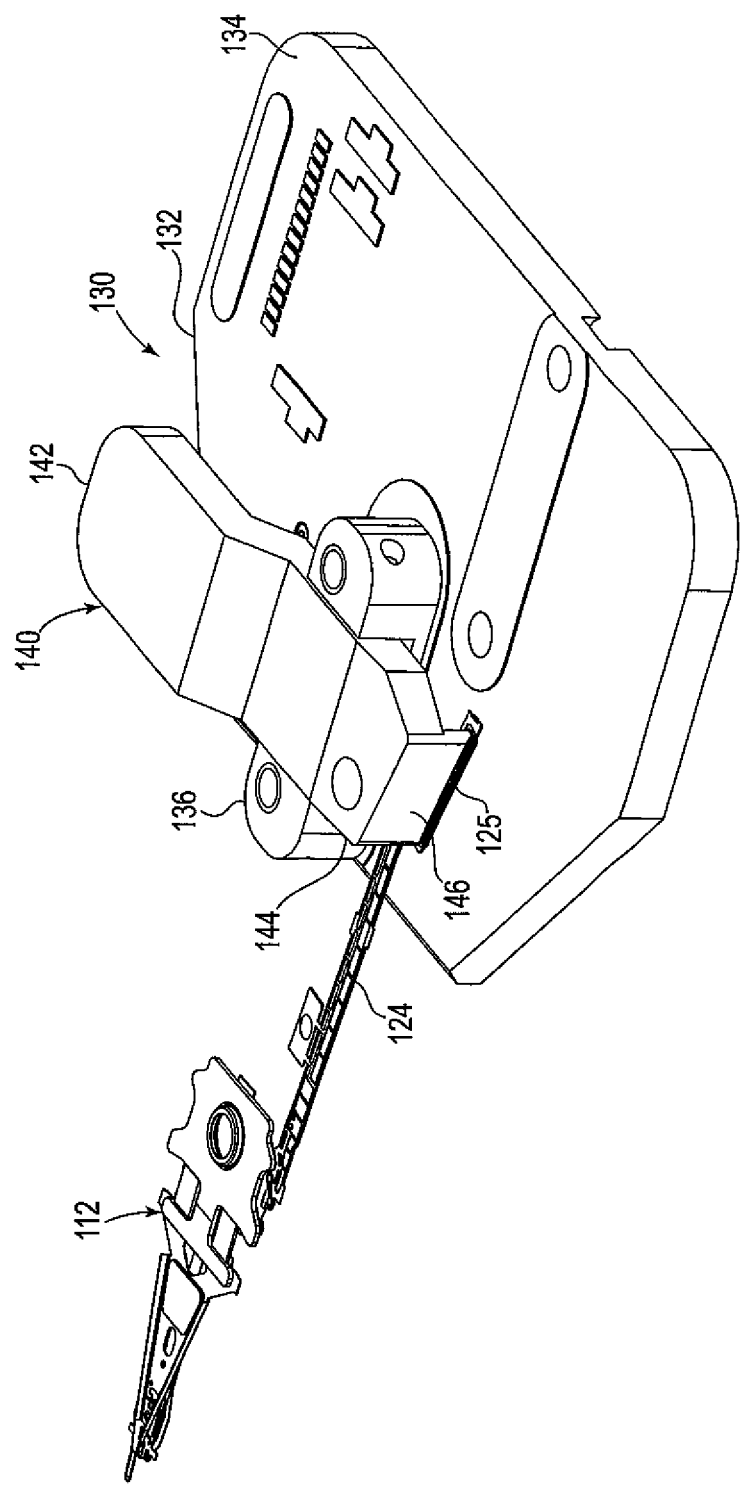
FIG. 3 is a perspective view of a testing fixture with the HGA engaged therein.
Figure 4:
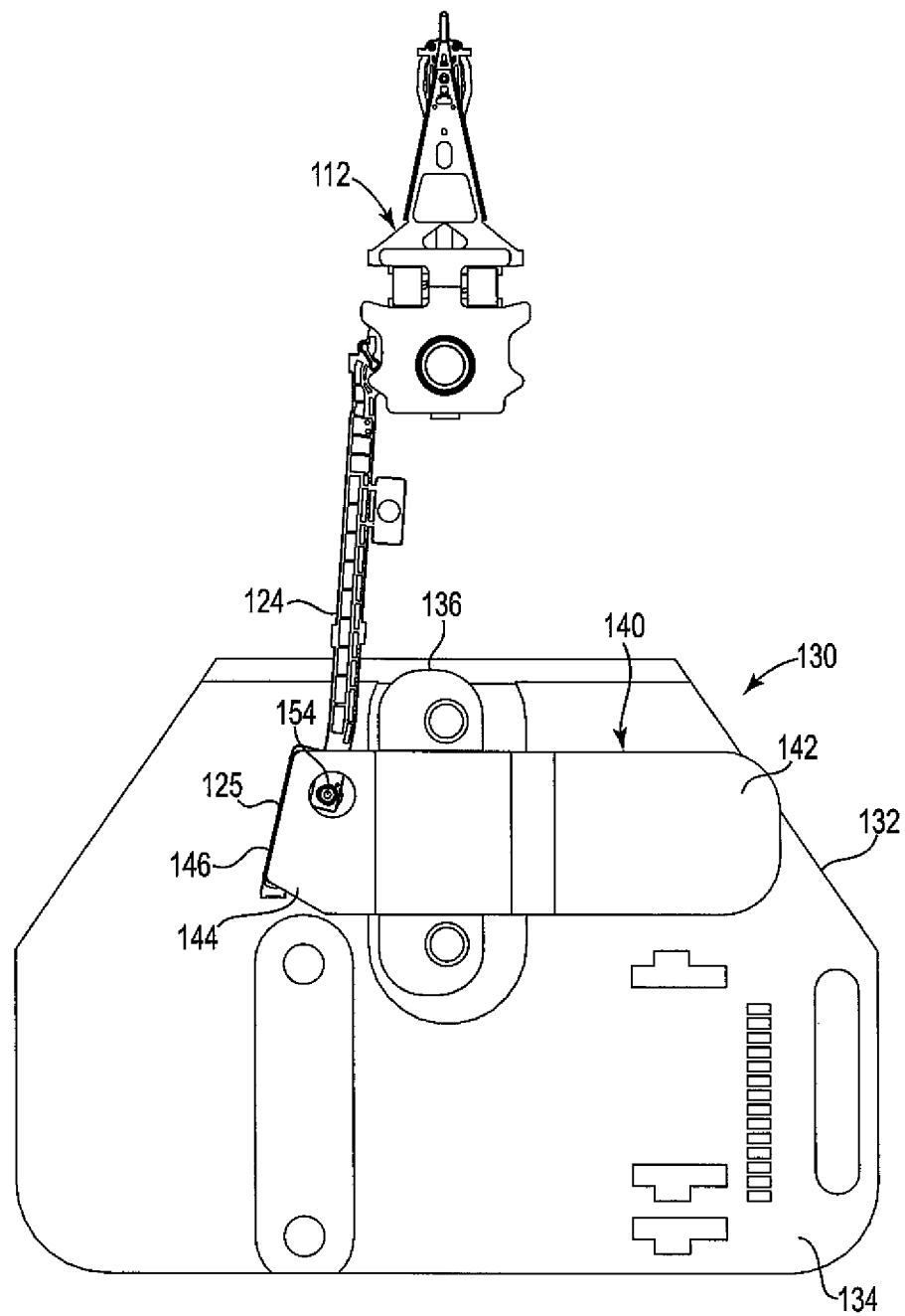
FIG. 4 is a top plan view of the testing fixture of FIG. 3 with the HGA engaged therein.
Figure 5:
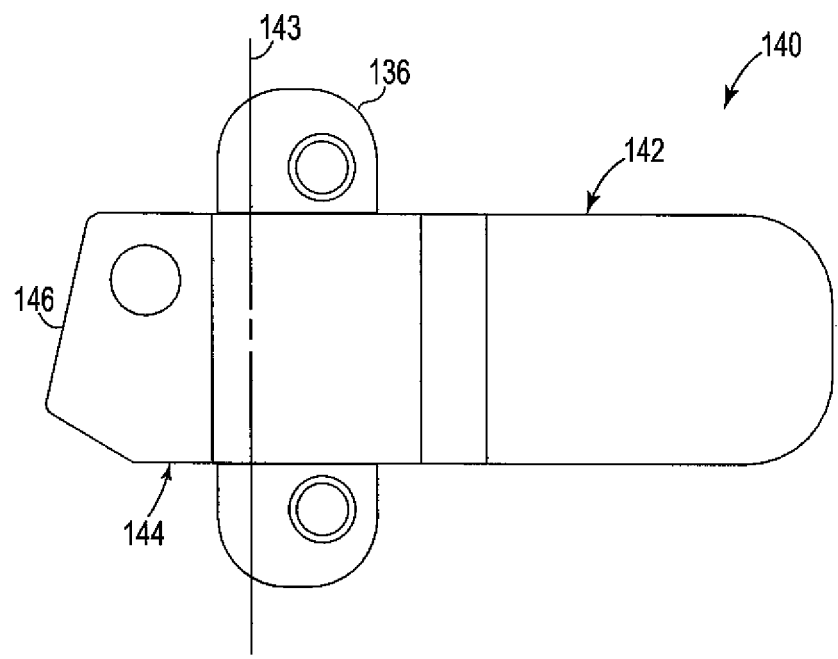
FIG. 5 is a top plan view of the clamping mechanism of the testing fixture of FIG. 3.
Figure 6:
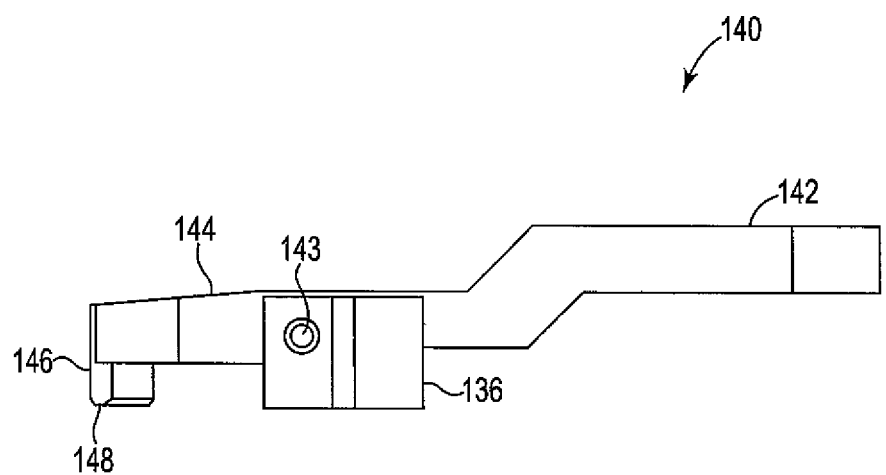
FIG. 6 is a side plan view of the clamping mechanism of FIG. 5.

A testing fixture 130, seen in FIGS. 3 and 4, has a base board 132 and a clamping mechanism 140, between which is held HGA 112 during testing. Clamping mechanism 140 is fixedly attached to top surface 134 of base board 132 by a pier 136. In some embodiments, clamping mechanism 140 is removably attached to pier 136 and/or pier 136 is removably attached to base board 132. FIGS. 5 and 6 illustrate additional details regarding clamping mechanism 140.

Clamping mechanism 140 has an activation portion 142 and an engagement portion 144, between which is a pivot axis 143; in some embodiments, pivot axis 143 is aligned with or in close proximity to a center of pier 136, whereas in other embodiments, pivot axis 143 is offset from the center of pier 136. Activation portion 142 provides a depressible area or surface for applying pressure to in order to pivot clamping mechanism 140 and thus move engagement portion 144 away from base board 132. Clamping mechanism 140 may be configured with a mechanism (e.g., coil spring, leaf spring) that holds activation portion 142 'up', thus holding engagement portion 144 'down,' close to or in contact with top surface 134 of base board 132.

Engagement portion 144 includes an end 146 and an engagement surface 148. In the illustrated embodiment, end 146 is orthogonal to the upper surface of engagement portion 144 and to engagement surface 148. Although not required, engagement surface 148 essentially follows the configuration (e.g., shape, alignment, position, etc.) of end 146. In the illustrated embodiment, best seen in FIG. 5, end 146 and thus engagement surface 148 is at an angle of approximately 15-20 degrees to pivot axis 143. In other embodiments, end 146 and engagement surface 148 are at an angle between 0 and 45 degrees to pivot axis 143; at an angle of 0, end 146 and engagement surface 148 would be parallel to pivot axis 143.

At least engagement surface 148 is a non-electrically conducting surface, such as an electrically insulating surface, and in some embodiments the entire end 146 is non-electrically conducting (e.g., electrically insulating). Alternately, the entire clamping mechanism 140 is non-electrically conducting (e.g., electrically insulating). When fixture 130 is in use, with flex circuit 124 positioned and engaged between end 146 and base board 132, engagement surface 148 will contact flex circuit 124, urging flex circuit 124 and circuit pad 125 against top surface 134 of base board 132.

Figure 7:
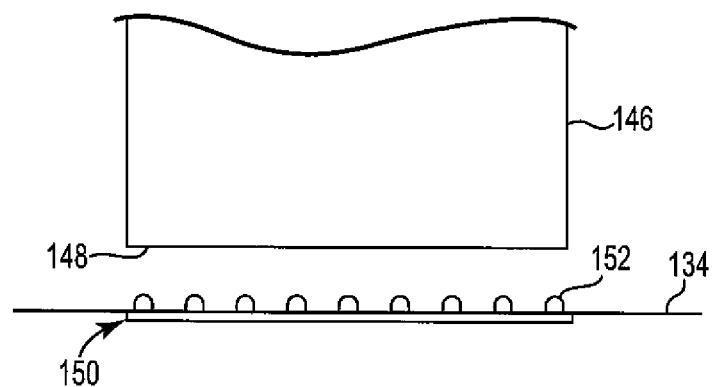
FIG. 7 is an enlarged side plan view of the testing fixture.

Present on top surface 134 of base board 132, directly below and surrounding the region directly below engagement surface 148 and end 146 is a contact region 150 (see FIG. 7); it is in contact region 150 that circuit pads 125 of flex circuit 124 contact top surface 134. Contact region 150 has a plurality of conductive contact points 152 composed of an electrically conductive material, such as gold (Au), silver (Ag), titanium (Ti), copper (Cu), platinum (Pt), alloy thereof or any combination thereof. An exemplary point 152 has a solid copper inner portion with a layer of gold on the outer surface. Typically, contact region 150 includes one contact point 152 for each circuit pad 125 of flex circuit 124, although in some embodiments, contact region 150 may include additional contact points 152.

Each contact point 152 has a structure at least 1 micrometer high and usually no more than 10 micrometers high, in some embodiments no more than 8 micrometers high, and in other embodiments no more than 6 micrometers high. The structure, at its widest dimension, has a diameter of at least 50 micrometers, in most embodiments at least 100 embodiments. In some embodiments, contact point 152 has a diameter of 200 to 300 micrometers; one particular example of a diameter for contact point 152 is 250 micrometers. In some embodiments, contact point 152 is a domed structure 2 to 10 micrometers high with a diameter of 100 to 500 micrometers, whereas in other embodiments the domed structure is 3 to 6 micrometers high with a diameter of 200 to 300 micrometers. Other suitable shapes for contact point 152 include cylinders and cubes, or shapes that have oval, rectangular, or any polygonal cross-section. Contact points 152 may have flat top surfaces or domed top surfaces, and may have sharp or rounded edges.

Contact points 152 are arranged to be electrically isolated from each other; that is, adjacent contact points 152 do not physically touch and are sufficiently far apart to avoid any stray current or voltage from one point 152 crossing over to an adjacent point 152. However, contact points 152 are spaced so that each contact point 152 aligns with a circuit pad 125 of HGA 112, which has minimal spacing between adjacent circuit pads 125, due to the desired to have a reduced size of HGA 112. In some embodiments, contact points 152 have a distance of no more than 500 micrometers between adjacent contact points 152, in other embodiments, no more than 450 micrometers therebetween. An exemplary distance between adjacent contact points 152 is about 430 micrometers.

In most embodiments, contact points 152 are linearly aligned, to form a straight line aligned with end 146 and engagement portion 144 of clamping mechanism 140. In other embodiments, contact points 152 may be jaggedly aligned, depending on the alignment of circuit pads 125. Similar to end 146 and engagement surface 148, contact points 152, or at least a central axis passing through the plurality of contact points 152, are aligned at an angle of approximately 15-20 degrees to pivot axis 143. In other embodiments, contact points 152 are at an angle between 0 and 45 degrees to pivot axis 143; at an angle of 0, contact points 152 would be parallel to pivot axis 143. In general, contact points 152 are configured to align with circuit pads 125 and with engagement surface 148 when HGA 112 is properly positioned on and held by fixture 130.

Returning to engagement surface 148, surface 148 may have a width similar to, the same as, slighting larger than, or slightly smaller than the largest dimension of contact points 152 (the largest dimension measured parallel to top surface 135 of base board 132). For example, engagement surface 148 may have a width of about 250 micrometers and contact points 152 may have a diameter of 200 to 300 micrometers. In most embodiments, the width of engagement surface 148 is no greater than 300 micrometers, in some embodiments no greater than 250 micrometers. The structure of end 146 may taper to the desired width of engagement surface 148; FIG. 6 shows an embodiment of the structure tapering to a blunt engagement surface 148.

Figure 8:
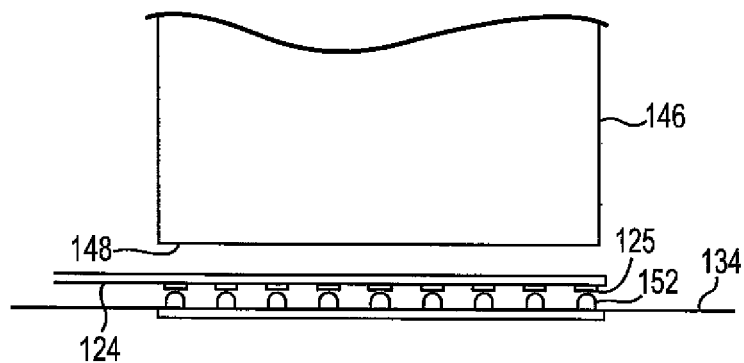
FIG. 8 is an enlarged side plan view of the testing fixture with an HGA positioned therein.

As indicated above, contact points 152 are positioned to engaged with circuit pads 125 when HGA 112 is properly positioned in and on testing fixture 130. In FIG. 8, an HGA is illustrated positioned in the testing fixture. Flex circuit 124 of the HGA is positioned between top surface 134 and engagement surface 148 with circuit pads 125 aligned with contact points 152.

Fixture 130 may include an alignment feature for facilitating properly alignment of flex circuit pad(s) 125 with contact points 152 and engagement surface 148. The alignment feature may be, for example, a pin configured to receive alignment hole 127 (FIG. 2). In FIG. 4, a pin 154 can be seen engaging the alignment hole through an aperture in engagement portion 144. In other embodiments, top surface 134 may have a recess in which the HGA sits, thus aligning flex circuit pad(s) 125 with contact points 152 and engagement surface 148.

Testing fixture 130 is used to dynamically test HGA 112, to confirm the electrical functionality of the circuits and of the read and write transducers and to identify any defective HGA 112. Fixture 130 may be used in the following manner to test an HGA. First, accessibility to the area above contact region 150 may be increased by opening or lifting end 146 and engagement surface 148 away from contact region 150 and points 152 by depressing activation portion 142, which pivots engagement portion 144 away from base board 132, thus increasing the area above contact region 150. HGA 112 is inserted between end 146 and contact region 150, and aligned so that flex circuit pads 125 of HGA 112 align with contact points 152. If present, alignment hole 127 of HGA 112 is engaged with alignment pin 154 on base board 132. After proper alignment of HGA 112, engagement surface 148 is brought into contact with HGA 112, for example by releasing activation portion 142. Engagement surface 148 provides sufficient force on flex circuit 124 of HGA 112 that circuit pads 125 form an electrical connection with contact points 152 of contact region 150. With electrical connection made, HGA 112 can be tested by appropriate means.

Thus, numerous embodiments of the FIXTURE FOR TESTING FLEXIBLE CIRCUIT are disclosed. The implementations described above and other implementations are within the scope of the following claims. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A test fixture for testing a head gimbal assembly having a flex circuit with a plurality of circuit pads, the fixture comprising:
   a contact board having a plurality of electrically conductive contact points on a surface thereof, the contact points arranged to contact the circuit pads of the flex circuit, each of the contact points comprising a gold surface and having a diameter and a height above the surface of the contact board of no more than 8 micrometers;
   a clamp assembly connected to the contact board, the clamp assembly having an activation end, an opposite engagement end, and a pivot axis extending orthogonal to an axis defined by the activation end and the engagement end;
   the engagement end having a non-conductive engagement surface configured to contact the head gimbal assembly on a surface opposite the plurality of circuit pads, the engagement surface extending at an angle between 0 and 45 degrees to the pivot axis and having a width the same as the diameter of the contact points.

2. The test fixture of claim 1, wherein the contact board further comprises a first alignment pin for engaging with an alignment aperture of the head gimbal assembly.

3. The test fixture of claim 1, wherein adjacent contact points have a distance of no more than 500 micrometers therebetween.

4. The test fixture of claim 1, wherein adjacent contact points have a distance of no more than 450 micrometers therebetween.

5. The test fixture of claim 1, wherein each of the plurality of contact points has a diameter of 200-300 micrometers.

6. The text fixture of claim 1, wherein the engagement surface extends at an angle between 10 and 25 degrees to the pivot axis.

7. A test fixture for testing a head gimbal assembly having a flex circuit with a plurality of circuit pads, the fixture comprising:
   a contact board having a plurality of electrically conductive contact points on a surface thereof, the contact points each having a diameter of 200-300 micrometers and comprising a dome structure comprising copper and a gold surface; and
   a clamp assembly connected to the contact board, the clamp assembly having an activation end, an opposite engagement end having a non-conductive engagement surface, and a pivot axis extending orthogonal to an axis defined by the activation end and the engagement end, the non-conductive engagement surface having a width of no more than 250 micrometers.

8. The test fixture of claim 7, wherein the contact points have an axis extending at an angle of between 0 and 45 degrees to the pivot axis.

9. The test fixture of claim 8, wherein the contact points have an axis extending at an angle of between 10 and 25 degrees to the pivot axis.

10. The test fixture of claim 7, wherein the contact points are aligned on an axis.

11. The test fixture of claim 7, wherein the non-conductive engagement surface comprises a polymeric material.

12. The test fixture of claim 11, wherein the activation end of the clamp assembly comprises the polymeric material.

13. The test fixture of claim 7 wherein engagement end comprises the engagement surface with a width of no more than 250 micrometers and a tapered portion.

14. The test fixture of claim 7, wherein adjacent contact points have a distance of no more than 500 micrometers therebetween.

15. The test fixture of claim 7, wherein each contact point has a diameter of 200-300 micrometers.

16. A test fixture for testing a head gimbal assembly having a flex circuit with a plurality of circuit pads, the fixture comprising:
   a contact board having a plurality of electrically conductive contact points on a surface thereof, the contact points comprising a dome structure comprising a gold surface; and
   a non-conductive clamp assembly pivotally connected to the contact board, the clamp assembly having an activation end, an opposite engagement end having an engagement surface, and a pivot axis extending orthogonal to an axis defined by the activation end and the engagement end;
   wherein adjacent contact points have a distance of no more than 500 micrometers therebetween, and wherein each of the contact points has a diameter of 200-300 micrometers.

17. The test fixture of claim 16, wherein adjacent contact points have a distance of no more than 450 micrometers therebetween.

18. The test fixture of claim 16, wherein each of the plurality of contact points has a diameter of 250 micrometers.

19. The test fixture of claim 16 wherein the engagement surface extends at an angle between 0 and 45 degrees to the pivot axis.

20. A test fixture for testing a head gimbal assembly having a flex circuit with a plurality of circuit pads, the fixture comprising:
   a contact board having a plurality of electrically conductive contact points on a surface thereof, the contact points arranged to contact the circuit pads of the flex circuit, the contact points each comprising a dome structure comprising copper and a gold surface, having a height of no more than 8 micrometers, a diameter of 200-300 micrometers, and a distance between adjacent contact points of more than 500 micrometers; and
   a clamp assembly pivotally connected to the contact board, the clamp assembly having an activation end, an opposite engagement end having a non-conductive engagement surface, and a pivot axis extending orthogonal to an axis defined by the activation end and the engagement end, the non-conductive engagement surface having a width of no more than 250 micrometers and extending at an angle between 10 and 25 degrees to the pivot axis.

* * * * *